United States Patent [19]
Lischewski et al.
[11] 4,282,154
[45] Aug. 4, 1981

[54] TAGGED GIBBERELLINS

[75] Inventors: Manfred Lischewski, Halle-Neustadt; Habil. G. Adam, Halle Isaale, both of German Democratic Rep.

[73] Assignee: Akademie der Wissenschaften DER, Berlin, German Democratic Rep.

[21] Appl. No.: 24,781

[22] Filed: Mar. 28, 1979

[30] Foreign Application Priority Data

Apr. 13, 1978 [DD] German Democratic Rep. ... 204769
Apr. 13, 1978 [DD] German Democratic Rep. ... 204771
Sep. 12, 1978 [DD] German Democratic Rep. ... 207758

[51] Int. Cl.$^3$ .......... C07D 307/77
[52] U.S. Cl. .......... 260/343.3 G; 71/89
[58] Field of Search .......... 260/343.3 G

[56] References Cited

PUBLICATIONS

Murofushi et al., Agric. Biol. Chem., 38(2), 475–476, 1974, S583 A37.
Murofushi et al., Agric. Biol. Chem., 41(6), 1075–1079, 1977, S583 A37.

*Primary Examiner*—John D. Randolph
*Assistant Examiner*—Jane T. Fan
*Attorney, Agent, or Firm*—Michael J. Striker

[57] ABSTRACT

As per invention, [6—$^3$H] or [6—$^2$H] gibberellins respectively are produced. By the process as per invention, production of tagged gibberellins is made from natural gibberellins or gibberellin derivatives having a carboxyl group at position 6 of the ent-gibberellin basic skeleton. After transformation into a gibberellin derivative with a hydroxymethyl group at position 6, oxidation is made to gibberellin-7-aldehyde with subsequent conversion of same to a mixture of 6-epimeric gibberellin-7-aldehydes, which will be obtained tagged at the C-6 position if deuterium or tritium donors are present during epimerization, oxidation into tagged gibberellins being performed thereafter.

By the invention, tagged gibberellins are made available which are tritiated or deuterated to such a C-H bond as is present in unsubstituted state in all natural gibberellins and their derivatives, and at which bond no biochemical changes have hitherto been observed.

The process as per invention is of general applicability and produces the tagged gibberellins with a high yield. The process is particularly suitable for compounds with acid-sensitive structure characteristics, for example with simultaneous presence of a hydroxyl group at the C-13 position and of a $\Delta$ 16.17 double bond.

13 Claims, No Drawings

TAGGED GIBBERELLINS

The invention concerns tagged gibberellins and their production.

Tagged compounds are such that are tritiated or deuterated. Gibberellins are to be understood as natural gibberellins and gibberellin derivatives that have a carboxyl group in position 6 of the ent-gibberellan basic skeleton; (in general, the ent-gibberellan nomenclature is used). With gibberellin derivatives the ent-gibberellan basic skeleton is intact or slightly modified; (f.i. seco-, homo-, nor- or dinor-ent-gibberellan, in given instances epimerized and/or containing multiple bonds) and, in given instances substituted in the most varied ways.

FIELD OF APPLICATION OF THE INVENTION

Tagged gibberellins are, in the first instance, fine biochemicals. The use of tagged gibberellins is significant in various fields, f.i. for biotechnological and analytical processes, for investigations of biosynthesis, metabolism, transportation, distribution, effects, and for the structure-activity analysis of these phytohormones and their partially synthetic structure analogues as basis for the synthesis of new active agents.

CHARACTERISTICS OF KNOWN TECHNICAL SOLUTIONS

Individual tritium-tagged gibberellins are known. They are produced by specific processes, the applicability of which is, however, restricted to tritiating of gibberellins with very specific structure characteristics. The tagging positions are located at C-1, C-2, C-3, C-6 and C-17 respectively of the ent-gibberellan basic skeleton. For instance, [1-$^3$H]-gibberellin-$A_5$ can be obtained from 3-methanesulfonylgibberellin-$A_3$-methylester, [1-$^3$H]-gibberellin-$A_8$ from [1-$^3$H]-gibberellin-$A_5$, [2, 3-$^3$H]-gibberellin-$A_{20}$ from gibberellin-$A_5$-methylester-16, 17-epoxide[N. MUROFUSHI, R. C. DURLEY and R. P. PHARIS, Agric. Biol. Chem. 41, 1075 (1977) and 38, 475 (1974)]. Further tagged gibberellins known, are [2,3-$^3$H]-gibberellin-$A_9$ [T. YOKOTA, D. R. REEVE and A. CROZIER, Agric. Biol. Chem. 40, 2091 (1976)], [1,2-$^3$H]-gibberellin-$A_1$ [H. KENDE, Plant Physiol. 42, 1012 (1967); P. W. PITEL, L. C. VINING, Canad. J. Biochem. 48, 259 (1970), A. MUSGRAVE, H. KENDE, Plant Physiol. 45, 56 (1970); R. NADEAU and L. RAPPAPORT, Phytochemistry 13, 1537 (1974)] and [1, 2-$^3$H]-gibberellin-$A_4$ [R. C. DURIEY and R. P. PHARIS, Planta 109, 357 (1973)]. In these compounds however, the tritium is in such positions where it can easily be substituted biochemically, f.i. in studies of biosynthesis or in investigations on metabolism.

It is furthermore known that preparation of $C_{20}$-gibberellins and their derivatives respectively, with the carboxyl group in the 6-position, can be accomplished by chemical methods starting from $C_{20}$-gibberellin-7-aldehydes or their derivatives respectively, in the presence of JONES reagent [J. R. BEARDER, J. MacMILLAN and B. O. PHINNEY, Phytochemistry 12, 2173 (1973); E. FUJITA, M. NODE and H. HORI, J. chem. Soc. Chem. Comm. 1975, 898 and J. chem. Soc., Perkin I 1977, 611]. In this way, gibberellin $A_{12}$ tagged in position 6 could also be obtained. This process is, however, not of general applicability, especially not with compounds having acid-sensitive structure characteristics, for instance in the simultaneous presence of a hydroxyl-group at the C-13 position and a $\Delta^{16.17}$ double bond.

With the aid of special processes, [17-$^3$H]-gibberellin-$A_9$ [D. M. REID, M. S. TUING, R. C. DURLEY and I. D. RAILTON, Planta 108, 67 (1972)] can be represented and [6-$^3$H]-gibberellin-$A_{12}$-7-aldehyde can be transformed microbially into [6-$^3$H]-gibberellin-$A_{14}$ (P. HEDDEN, J. MacMILLAN and B. O. PHINNEY, J. chem. Soc. Perkin I 1974, 587).

The production of some gibberellin-7-aldehydes has also been described already. Thus, gibberellin-7-aldehydes are known that have an aldehyde group at the natural 6β-position of the ent-gibberellan basic skeleton [M. LISCHEWSKI and G. ADAM, GDR-Letters Patent 112 758; M. LISCHEWSKI and G. ADAM, Tetrahedron Letters 2835 (1974); M. LISCHEWSKI and G. ADAM, GDR-Letters Patent 120 875; M. LISCHEWSKI and G. ADAM, Tetrahedron Letters 2569 (1975); M LISCHEWSKI and G. ADAM, Z. Chem. 16, 486 (1976); J. R. HANSON and J. HAWKER, J. chem. Soc. Chem. Comm. 1971, 208 and Phytochemistry 12, 1073 (1973); B. E. CROSS, K. NORTON and J. C. STEWART, J. chem. Soc. (C) 1968, 1054; B. E. CROSS and I. L. GATFIELD, ibid. 1971, 1539]. They are produced via gibberellin anhydrides or gibberellin alcohols i.e. gibberellin derivatives with a hydroxymethyl group at the 6-position. The gibberellin-7-aldehydes however, will develop in the first-named instance with only a low yield and are furthermore difficult to isolate, so that the aldehydes are instantaneously reduced to gibberellin-7-alcohols. In the second instance, an undesirable by-product will develop.

Gibberellin-7-aldehydes having an aldehyde group in the epimeric 6α-position have not yet become known.

Reproduction of several tagged gibberellin-7-aldehydes with an aldehyde group in the 6-position has also been reported. Product of [6-$^3$H]- or [6-$^2$H]-gibberellin-$A_{12}$-aldehyde and gibberellin-$A_{14}$-aldehyde has been described [J. R. BEARDER, J. MacMillan and B. O. PHINNEY, Phytochemistry 12, 2173, 2615 (1973); J. H. GRAEBE, P. HEDDEN AND J. MacMILLAN, J. chem. Soc. Chem. Comm. 1975, 161; P. HEDDEN, J. MacMILLAN and B. O. PHINNEY, J. chem. Soc., Perkin I 1974, 587]. On account of its severe conditions (long reaction times, large excess of bases, increased temperatures), this process is applicable only to these base-stable gibberellin-7-aldehydes and will return only moderate yields.

Furthermore, the synthesis of [7-$^3$H, 17-$^{14}$-C]-gibberellin-$A_{12}$-aldehyde is known, [B. DOCKERILL, R. EVANS and J. R. HANSON, J. chem. Soc. Chem. Comm. 1977, 919]. Such gibberellin-7-aldehydes tritiated in Position 7 are of the disadvantage that the tritium will be removed on biosynthetic or chemical transformation of the 7-aldehyde function to a carboxyl group.

OBJECTIVE OF THE INVENTION

It is the objective of the invention to make available tagged gibberellins and to develop a process for their production which will bring good yields and be of general applicability.

EXPLANATION OF THE NATURE OF THE INVENTION

The task of the invention consists in making available gibberellins tritiated or deuterated to such a C—H bond as is present in unsubstituted form in all natural gibberellins and their derivatives, and in which no biochemical changes have so far been observed, this in order to ensure a wide band of applicability for the production process.

As per invention, [6-$^3$H] and [6-$^2$H]-gibberellins respectively, are produced.

According to the process as per invention, production of tagged gibberellins is made from natural gibberellins or gibberellin derivatives having a carboxyl group at position 6 of the entgibberellan basic structure. Initially, the corresponding gibberellin alcohol i.e. a gibberellin derivative with a hydroxymethyl group at position 6 is obtained in the known manner for these primary products, [M. LISCHEWSKI and G. ADAM, GDR-Letters Patent 112 753 of 22 May 1974; M. LISCHEWSKI and G. ADAM, GDR-Letters Patent 121 784 of 4 July 1975; M. LISCHEWSKI and G. ADAM, Tetrahedron Letters 2835 (1974); M. LISCHEWSKI and G. ADAM, Tetrahedron Letters 3691 (1975); M. LISCHEWSKI and G. ADAM, Z. Chem. 16 (1976), 486]. Oxydation to gibberellin-7-aldehyde as per invention is subsequently made, thereupon conversion to a mixture of 6-epimeric gibberellin-7-aldehydes which, in the presence of deuterium or tritium donors during epimerization, are obtained, tagged at the C-6 position, and are then oxidized to tagged gibberellins. According to the process as per invention, $C_{19}$-as well as tagged $C_{20}$-gibberellins can be produced.

As per invention, oxydation to the aldehyde ensues with the aid of a chromium-bearing oxydant, f.i. chromic (VI) oxide, pyridinium chlorochromate or the chromium peroxide-pyridine complex ($CrO_5$ . Py), in a solvent which will not oxidize under the applied conditions, such as methylene chloride or chloroform. The temperature of the reaction can herein be varied within a wide range. Working at room temperature will best answer the purpose. When using gibberelins with further hydroxyl groups sensitive to oxydation, it is of advantage to provide these with a protective group prior to oxidation. As protective groups acyl groups, such as acetyl, propionyl or benzoyl, silyl groups such as trimethylsilyl, or the tetrahydropyranyl can, for instance, be applied. As an example, the hydroxyl group in 6$\beta$-hydroxymethyl-7-nor-gibberellin-$A_3$ or in 6$\beta$-hydroxymethyl-7-nor-gibberellin-$A_1$ at the C-3 position, must be protected in this manner. Concluding treatment is made by the usual methods, for instance by column chromatography using organic solvents. The process is of general applicability and will produce the desired gibberellin-7-aldehydes with a high yield and without by-products.

As per invention, conversion to a mixture of 6-epimeric glbberellin-7-aldehydes is accomplished by enolizing with a base, gibberellin-7-aldehydes that have an aldehyde group at the 6$\alpha$ or 6$\beta$ position, and adding compounds with deuterium or tritium donor properties.

The epimeric mixture consists of a gibberellin-7-aldehyde with an aldehyde group in position 6$\alpha$, and a gibberellin-7-aldehyde with an aldehyde group in position 6$\beta$, wherein upon the application of compounds with deuterium or tritium donor properties, both epimers obtained are tagged at the C-6 position. This work is done in an organic solvent, f.i. abs. tetrahydrofuran or abs. dioxane, under the exclusion of air, f.i. in an argon or nitrogen atmosphere. Strong bases, but neucleophil only to a small extent, are preferably used. Of particular advantage are alkaline amides especially such with space-filling organic radicals, f.i. lithium-diisopropylamide, lithium-2, 2, 6, 6-tetramethylpiperidide or hydrides, particularly potassium hydride. If gibberellin-7-aldehydes are reacted without acidic hydrogen atoms (f.i. gibberellin-$A_9$-7-aldehyde), the base required for enolization will be required only in equivalent amounts or in a small excess (f.i. 1.1 equivalents). When using gibberellin-7-aldehydes with acidic hydrogen atoms (f.i. gibberellin-7-aldehydes containing hydroxyl or carboxyl groups), it will be of advantage to substitute these hydrogen atoms. As protective groups for hydroxyl groups, the trimethyl silyl group, the tert. butyl-dimethylsilyl group or the tetrahydropyranyl group can, for instance, be used. Carboxyl groups, however, will be esterified, or neutralized by bases that are present in excess. Enolation of gibberellin-7-aldehydes in the presence of aciduous hydrogen atoms is possible. This will, however, require more base equivalents in order to enable the formation of enolate.

As compounds with the properties of hydrogen, deuterium or tritium donors (hereafter called hydrogen, deuterium, or tritium donors) the most varying compounds with exchangeable hydrogen, deuterium or tritium are suitable, for example $H_2O$, $^2H_2O$, $^3H_2O$, H-OR, $^2$H—OR, $^3$H—OR, wherein R stands for a substituted or unsubstituted alkyl, aryl, or acyl grouping, and also for organic or inorganic acids.

When using acids, the resultant gibberellin-7-aldehydes are not exposed to alkaline or nucleophilic conditions, which is of special importance for the production of base-unstable gibberellin-7-aldehydes.

Irrespective of proceeding for the tagging of a gibberellin-7-aldehyde with an aldehyde group in position 6$\beta$ or one in position 6$\beta$, one will always obtain tagged gibberellin-7-aldehydes with an aldehyde group in position 6$\beta$ as well as tagged gibberellin-7-aldehydes with an aldehyde group in position 6$\alpha$.

During the formation of enolate and also during the reaction with hydrogen, deuterium, or tritium donors, the temperature can be varied through a wide range. Working temperatures between $-78°$ C. and room temperature will be appropriate.

Concluding treatment of the products of reaction is made by the usual methods, f.i. by column chromatography, using the customary solvents. It is worth noting that both epimers developing during the process as per invention, are distinguished by their readily allowing chromatographic separation.

The process as per invention is of general applicability to gibberellin-7-aldehyde, wherein structure characteristics pertaining to base instability are not changed. This process allows for the first time access to non-tagged or tagged gibberellin-7-aldehydes with an aldehyde group in the 6 position. The mild conditions of conducting the reaction make the process as per invention suitable for the epimerization and tagging also of $C_{19}$-gibberellin-7-aldehydes with 19→10 lactone ring. As an example, [6-$^3$H] respectively [6-$^2$H]-gibberellin-$A_1$-7-aldehyde, -gibberellin-$A_3$-7-aldehyde, -gibberellin-$A_4$-7-aldehyde, -gibberellin-$A_5$-7-aldehyde, -gibberellin-$A_7$-7-aldehyde are now accessible, which hitherto could not be produced by another method.

Furthermore, known tagged gibberellin-7-aldehydes, f.i. [6-$^3$H]-gibberellin-$A_{12}$-aldehydes can be synthesized by the process as per invention with yields higher than previously described.

Preparation of double-tagged gibberellin-7-aldehydes is also possible by the process as per invention. In this way, for instance, it is possible to produce [17-$^{14}$C, 6-$^3$H]-gibberellin-$A_3$-7-aldehyde and [17-$^{14}$C, 6-$^3$H]-6-epigibberellin-$A_3$-7-aldehyde from [17-$^{14}$C]-gibberellin- $A_3$-7-aldehyde, [1-$^3$H, 6-$^3$H]-gibberellin-$A_5$-7-aldehyde and [1-$^3$H, 6-$^3$H]-6-epigibberellin-$A_5$-7-aldehyde from [1-$^3$H]-gibberellin-$A_5$-7-aldehyde, and also [6-$^3$H, 15-$^3$H]-gibberellin-$A_3$-7-aldehyde and [6-$^3$H, 15-$^3$H]-6-epigibberellin-$A_3$-7-aldehyde from [15-$^3$H]-gibberellin-$A_3$-7-aldehyde.

It is characteristic for the tagged gibberellin-7-aldehyde produced as per invention that a tag with stability and high specific radioactivity can be attained.

The tagged gibberellin-7-aldehydes, obtained after epimerization, can, as per invention, be oxydized under mild conditions to the respective tagged gibberellins or gibberellin-derivatives with a carboxyl group at the 6 position. As mild conditions, the presence of a strong acid is especially understood in this instance.

The most variegated media can be used as oxydants as, f.i. chromiumbearing compounds, especially chromic (VI)-oxide, peroxo compounds, f.i. perbenzoic acid, atmospheric hydrogen, in given instances under the influence of salts of heavy metals such as manganese or cobalt salts. Oxidation is performed in a solvent which, under the conditions as applied will not oxidize, preferably a tertiary amine, wherein pyridin is of particular advantage.

The temperature of the reaction can be varied through a wide range, wherein work at room temperature is most appropriate.

When using gibberellin compounds with hydroxyl groups sensitive to oxidation, it is of advantage to provide them with a protective group prior to oxidation. Protective groups applied are f.i. acyl groups such as acetyl, propionyl or benzoyl, silyl groups such as trimethylsilyl or the tetrahydropyranil group. The hydroxyl group in the gibberellin-$A_3$-7-aldehyde or gibberellin-$A_1$-7-aldehyde at the C-3 position can be protected in this way.

Concluding treatment of the products of reaction is made by the customary methods, for example, by column chromatography using organic solvents.

The process as per invention is of general applicability and will provide a high yield of the desired gibberellin compounds with the carboxyl group at the 6-position, from gibberellin-7-aldehydes. The process is particularly suitable for gibberellin-7-aldehydes in which a hydroxyl group at the C-13 position and a $\Delta^{16.17}$-double bond are simultaneously present. The process as per invention is also usable for non-tagged compounds.

It is characteristic for the tagged gibberellins produced by this process that the tag is stable and can be attained with a high specific radioactivity. Since, on one hand the tagging can be proved or localized respectively with extreme ease, and on the other, is situated at a position where hitherto no biochemical mutations have been observed, these compounds are of outstanding suitability, for instance, in studies of biosynthesis or investigations of metabolism.

The following examples will explain the invention, wherein, however, the special conditions as noted are not restricting the invention and the conditions of the reaction can also be applied in the production of other compounds.

EXAMPLES OF REALIZATION

EXAMPLE 1

3.46 g (10 mmol) gibberellin-$A_3$(I) are acetylated by the known method with 20 ml acetic anhydride in 20 ml abs. pyridin. After standing for one week at room temperature, concentration is made and chromatography performed. With chloroform as eluting medium, 3.65 g $\hat{=}$ 85% of the theoretical value, are obtained of 0(3), 0(13)-diacetyl-gibberellin-$A_3$(II).

To 1.722 g (4 mmol) 0(3), 0(13)-diacetyl-gibberellin-$A_3$(II), dissolved in 10 ml abs. THF and 10 ml abs. dioxane, 413 mg (2 mmol) dicyclohexylcarbodiimide are added at −15° C. After standing for 12 hours, filtration is made from dicyclohexylurea and the solution is combined with 454 mg (12 mmol) $NaBH_4$. The reaction is allowed to proceed for two hours, then 2 ml glacial acetic acid are added and concentration in vacuum is made thereafter. After adding ether, this is shaken out 10 times with a saturated solution of $NaHCO_3$. The residue of the ether phase dried with $NaSO_4$, is chromatographed, during which treatment, elution with chloroform yields 566 mg $\hat{=}$ 68% of the theoretical value, of 0(13)-diacetyl-6β-hydroxymethyl-7-nor-gibberellin-$A_3$(III).

The acidulated aqueous phases will yield, after extraction with ether and chromatography with chloroform as eluting medium, 690 mg $\hat{=}$ 80% of the theoretical value, of 0(3), 0(13)-diacetyl-gibberellin-$A_3$(II).

To 431.2 mg (2 mmol) pyridinium chlorochromate in 5 ml dry $CH_2Cl_2$, a solution 416 mg (1 mmol) 0(3), 0(13)-diacetyl-6β-hydroxymethyl-7-nor-gibberellin-$A_3$(III) in 5 ml of dry $CH_2Cl_2$ is dripped in at 15° C., under stirring and under an argon atmosphere. After two hours, the mixture is combined with 50 ml ether. After separation of the ether phase, the residue is still extracted with ether several times. The combined ether extracts are eluted with water, dried with $Na_2SO_4$ and concentrated in vacuum. Subsequent chromatography of the residue with yield on elution with n-hexane/-chloroform 4:6 vol/vol 338 mg $\hat{=}$ 87% of the theoretical value (yield calculated relative to reacted alcohol compound) of 0(3), 0(13)-diacetyl-gibberellin-$A_3$-7-aldehyde(IV): m.p.: 162°–164° C. (ether/n-hexane); $[\alpha]_D^{25}$+204.8° (c=0.54—abs. dioxane); MS=m/e 414 ($M^+$ respi $M^-$); IR($CHCl_3$): $\nu_{max}$ 2820, 2725 and 1725 (aldehyde), 1775 (γ-lactone-CO), 1740 (ester-CO), 1665 (=$CH_2$), 1635 (—CH=CH—) and 1255 $cm^{-1}$ (acetyl).

On elution with chloroform, 26 mg of unconverted 0(3), 0(13)-diacetyl-6β-hydroxymethyl-7-nor-gibberellin-$A_3$(III), are furthermore obtained.

414.5 mg (1 mmol) 0(3), 0(13)-diacetyl-gibberellin-$A_3$-7-aldehyde are combined with 10 ml of a solution of 0.2 n $NaOCH_3$. After standing for 3 hours at room temperature, acidulation is made with glacial acetic acid, concentration effected in vacuum and the residue, dissolved in ethyl acetate, is shaken out with a saturated solution of $NaHCO_3$. Drying of the ethyl acetate phase with $Na_2SO_4$, concentrating in vacuum, and chromatography, will yield, on elution with chloroform, 34 mg of 0(13)-acetyl-gibberellin-$A_3$-7-aldehyde, and with a gradient of chloroform/ethyl acetate 8:2 vol/vol, 227 mg $\hat{=}$ 75% of the theoretical value, are obtained of gibberellin-$A_3$-7-aldehyde (V):

Melting point 172°–175° C. (from acetone-n-hexane); $[\alpha]_D^{25}$+118.8° (c=0.61—ethanol);

MS: m/e 330, 1433 ($M^+$, $C_{19}H_{22}O_5$ ber. 330, 1468);

IR ($CHCl_3$): $\nu_{max}$ 3610 (OH), 2725, 2820 and 1725 (aldehyde), 1775 (γ-lactone-CO) and 1635 $cm^{-1}$ (—CH=CH—); 100 MHz-$^1$H-NMR: $\delta_{TMS}^{aceton\text{-}D6}$ 1, 14 (s, 18—$H_3$), 2.279 (dd, J=10.5 Hz and J'=2.5 Hz, 6-H), 3.29 (d, J=10.5 Hz, 5-H), 4.06 (d, J=3.5 Hz, 3-H), 4.93 and 5.24 (m, 17-$H_2$), 5.90 (dd, J=9.5 Hz and J'=3.5 Hz, 2-H), 6.39 (d, J=9.5 Hz, 1-H) and 9.84 ppm (d, J=2.5 Hz, 7H).

To 330.4 mg (1 mmol) gibberellin-$A_3$-7-aldehyde(V), dissolved in 15 ml absolute pyridin, 2 ml hexamethyldisilazane and 2 ml trimethyl chlorsilane are added. This is left standing at room temperature for three hours and concentrated in vacuum. After addition of a saturated solution of $NaHCO_3$ thorough shaking out with ether is made. The combined ether phases are dried with anhydrous $MgSO_4$ and concentrated in vacuum.

The residue is left standing overnight in vacuum over $P_4O_{10}$. Subsequently, the silylated gibberellin-$A_3$-7 aldehyde is dissolved under argon in 8 ml oxygen-free and absolute THF and 44 mg (1 mmol) potassium hydride are added. After stirring for one hour at room temperature, 0.1 ml (5.55 mmol) $^3H_2O$ (specific radioactivity 3 mCi/mmol) are added to the enolate. Stirring is continued for a further three minutes and combination with 1 ml glacial acetic acid, is then made.

Repeated concentration in vacuum, with adding of methanol, makes possible the removal of unstable tritium. To separate the protective groups, 8 ml THF, 2 ml $H_2O$, and 1 ml glacial acetic acid are added to the residue which is left standing overnight. After concentration in vacuum, a saturated solution of $NaHCO_3$ is added and shaking out with ethyl acetate is performed for several times. Drying of the organic phase with $Na_2SO_4$ and concentration in vacuum will produce a residue that is subsequently chromatographed. Elution with chloroform (fractions 1–35), chloroform/ethyl acetate 9:1 vol/vol (fractions 36–58), chloroform/ethyl acetate 8:2 vol/vol (fractions 59–92) and chloroform-/ethyl acetate 7:3 vol/vol (fractions 93–150) will yield, on combining the fractions 65–88, 99 mg=30% of the theoretical value, [6-$^3$H]-gibberellin-$A_3$-7-aldehyde(VI), and on joining the fractions 95–148, 145 mg ≙ 44% of the theoretical value [6-$^3$H]-6-epigibberellin-$A_3$-7-aldehyde (VII). [6-$^3$H]-gibberellin-$A_3$-7-aldehyde(VI):

Specific radioactivity 1.37 mCi/mmol;
Melting point: 172°–175° C.;
$[\alpha]_D^{25}+117.9°$ (c=0.58—ethanol);
MS: m/e 330 (M+ resp. M−).

[6-$^3$H]-6-epigibberellin-$A_3$-7-aldehyde(VII):
Specific radioactivity 1.47 mCi/mmol;
Melting point: 185°–187° C. (from aceton/n-hexane);
$[\alpha]_D^{26}+2.4°$ (c=0.35—ethanol);
MS: m/e 330 (M+ resp. M−); IR ($CHCl_3$): $\nu_{max}$3600 (OH), 2730 and 1725 (aldehyde), 1775 (γ-lactone-CO) and 1665 $cm^{-1}$ (=$CH_2$); 100 MHz-$^1$H-NMR: $\delta_{TMS}^{aceton-D6}$ 1, 19 (s, 18-$H_3$), 2.75 (dd, J=10 Hz and J'=2.5 Hz, 6-H), 2.97 (d, J=10 Hz, 5-H) 4.32 (m, 3-H), 4.89 and 5.21 (m, 17-$H_2$), 5.84 (dd, J=9 Hz and J'=2.5 Hz, 2-H) 6.28 (dd, J=9 Hz and J'2 Hz, 1-H) and 9.80 ppm (d, J=2.5 Hz, 7-H).

330.4 mg (1 mmol) [6-$^3$H]-gibberellin-$A_3$-7-aldehyde(VI) (specific radioactivity 1.37 mCi/mmol) are acetylated with 3 ml acetic anhydride in 3 ml pyridin. After two hours, concentration in vacuum is made and the crude [6-$^3$H]-8(3)-acetyl-gibberellin-$A_3$-7-aldehyde is dissolved in 8 ml absolute pyridine and combined under stirring with 200 mg (2 mmol) $CrO_3$. After stirring for two hours, concentration is made in vacuum, ether added, and repeated shaking out with 2% HCl made. The residue of the ether phase, dried with $Na_2SO_4$ and concentrated, is then deacetylated with 10 ml of a 0.2 n solution of $NaOCH_3$. After 15 minutes standing at room temperature, acidulation is made with acetic anhydride, concentration made in vacuum, 2% HCl added, and extraction with ethyl acetate made. The residue is chromatographed after drying with $Na_2SO_4$ and concentration of the organic phase. Elution with chloroform/ethyl acetate 8:2 vol/vol, yields 49 mg unreacted [6-$^3$H] gibberellin-7-aldehyde. With a gradient chloroform/ethyl acetate 4:6 vol/vol, a yield is obtained of 236 mg ≙ 80% of the theoretical value, [6-$^3$H]-gibberellin-$A_3$(VIII):

Specific radioactivity 1.21 mCi/mmol;
Melting point: 233°–235° C. (from aceton/n-hexane);
$[\alpha]_D^{25}+84.2°$ (c=0.43—ethanol);
MS: m/e 346 (M+ resp. M−);
IR (Nujol): $\nu_{max}$3390 (br, OH), 1750 (γ-lactone-CO), 1715 (acid-CO) and 1660 $cm^{-1}$ (=$CH_2$).

For the oxydation of 330.4 mg (1 mmol) [6-$^3$H]-epigibberellin-$A_3$-7-aldehyde(VII) (specific radioactivity 1.47 mCi/mmol), acetylation is made with 3 ml acetic anhydride in 3 ml absolute pyridin. After two hours, concentration is made in vaccum and the crude [6-$^3$-H]-0(3)-acetyl-6-epigibberellin-$A_3$-7-aldehyde is dissolved in 8 ml absolute pyridine and combined under stirring with 300 mg (3 mmol) of $CrO_3$. After stirring for 18 hours, concentration in vacuum is made anew, ethyl acetated added, and repeated shaking out with 2% HCl performed. The residue of the organic phase, dried with $Na_2SO_4$ and concentrated, is then deacylated with with 10 ml of a 0.2 solution of $NaOCH_3$. After standing at room temperature for 15 minutes, acidulation is made with glacial acetic acid, then concentration, 2% HCl added and extraction performed with ethyl acetate. The residue is chromatographed after the organic phase has been dried with $Na_2SO_4$ and concentrated. On elution with chloroform/ethyl acetate 7:3 vol/vol, 53 mg [6-$^3$H]-6-epigibberellin-$A_3$-7-aldehyde(VII) are returned. With a gradient of chloroform/ethyl acetate 3:7 vol/-vol, elution will yield 125.1 mg ≙ 43% of the theoretical value, of 6-$^3$H]-6-epigibberellin-$A_3$(IX):

Specific radioactivity 1.30 mCi/mmol;
Melting point: 173°–175° C. (from ethyl acetate)
$[\alpha]_D^{28}-14.5°$ (c=0.39—ethanol);
MS: m/e 346 (M+ resp. M−);
IR (Nujol): $\nu_{max}$ 3400 (br, OH), 1755 (γ-lactone-CO) and
1720 $cm^{-1}$ (acid-CO); 100 MHz−$^1$H-NMR: $\gamma_{TMS'}^{ton-D6}$ 1,26 (s, 18-$H_3$), 2.64 (d, J=10 Hz, 6-H), 2.86 (d, J=10 Hz, 5-H), 4.32 (m, 3-H) 4.88 and 5.23 (m, 17-$H_2$), 5.83 (dd, J=9 Hz and J'=2.5 Hz, 2-H) and 6.27 ppm (dd, J=9 Hz and J'=1,5 Hz, 1-H).

EXAMPLE 2

Analogous to example 1, 330.4 mg (1 mmol) are silylated and enolized. Thereupon, 0.1 ml $^2H_2O$ (5.55 mmol; 99.9% purity) are added. Analogous concluding treatment and chromatography will yield 102.5 mg ≙ 31% of the theoretical value [6-$^2$H]-gibberellin-$A_3$-7-aldehyde(X) and 142.3 mg ≙ 43% of the theoretical value [6-$^2$H]-6-epigibberellin-$A_3$-7-aldehyde(XI). [6-$^2$H]-gibberellin-$A_3$-7-aldehyde(X): Melting point 172°–174° C. (from aceton/n-hexane); MS: m/e 331 (M+ or M−);

In the $^1$H-NMR-spectrum, the protons (5-H) and (7-H) appear as singlets and, as a consequence, the (6-$^2$H) is invisible.

[6-$^2$H]-6-epigibberellin-$A_3$-7-aldehyde(XI): Melting point 184°–187° C. (from aceton/n-hexane); MS=m/e 331 (M+ or M−);

In the $^1H$-NMR-spectrum, the protons (5-H) and (7-H) are also appearing as singlets, the ($6-^2H$) is missing.

Oxydation of [$6-^2H$]-gibberellin-$A_3$-7-aldehyde or [$6-^2H$]-6-epigibberellin-$A_3$-7-aldehyde respectively, will produce [$6-^2H$]-gibberellin-$A_3$(XII) or [$6-^2H$]-6-epigibberellin-$A_3$(XIII) respectively, analogous to example 1.

EXAMPLE 3

For epimerization, 330.4 mg (1 mmol) gibberellin-$A_3$-7-aldehyde(V) silylated analogous to example 1 and enolized thereafter. The enolate is then combined with 1 ml glacial acetic anhydride and 2 ml water, concluding treatment proceeding in an analogous manner. A yield is obtained of 143 mg=61% of the theoretical value, 6-epigibberellin-$A_3$-7-aldehyde(XIV) (96 mg gibberellin-$A_3$-7-aldehyde are returned).

Analogous oxidation of 330,4 mg (1 mmol) 6-epigibberellin-$A_3$-7-aldehyde (XIV) will yield 116 mg=41% of the theoretical value, 6-epigibberellin-$A_3$ (XV), and furthermore 60 mg of unreacted 6-epigibberellin-$A_3$-7-aldehyde.

EXAMPLE 4

330,4 mg (1 mmol) 6-epigibberellin-$A_3$-7-aldehyde (XIV), dissolved in 15 ml absolute pyridin, are combined with 2 ml hexamethyldisilazane and 2 ml trimethylsilane. Concentration is made after 3 hours standing at room temperature, saturated $NaHCO_3$ solution added, and repeated extraction with ether performed. The organic phase is subsequently dried with $MgSO_4$, concentrated in vacuum, and dried in vacuum over $P_4O_{10}$.

The silylated 6-epigibberellin-7-aldehyde is dissolved under argon in 8 ml oxygen-free and absolute THF, and 44 mg (1.1 mmol) potassium hydride are added at room temperature. After stirring for one hour at room temperature, 1 ml Methanol, 1 ml glacial acetic acid and 1 ml $H_2O$ are added to the enolate. After standing overnight, concentration is made and the residue chromatographed. Concluding treatment by chromatography yields 99 mg ≙ 54% of the theoretical value, gibberellin-$A_3$-7-aldehyde(V) (146 mg 6-epigibberellin-$A_3$-7-aldehyde(XIV) are returned). With analogous oxydation of 330.4 mg (1 mmol) gibberellin-$A_3$-7-aldehyde (V), 228 mg ≙ 78% of the theoretical value, gibberellin-$A_3$(I) are obtained (and furthermore 52 mg of unreacted gibberellin-$A_3$-7-aldehyde).

EXAMPLE 5

Analogous to example 4, 330.4 mg (1 mmol) 6-epigibberellin-$A_3$-7-aldehyde(XIV) are silylated and enolized. Thereafter, 0.1 ml $^3H_2O$ (specific radioactivity 3 mCi/mmol) are added. Analogous concluding treatment yields 103 mg ≙ 31% of the theoretical value [$6-^3H$]-gibberellin-$A_3$-7-aldehyde(VI) (specific radioactivity 1.5 mCi/mmol) and 148.3 mg ≙ 45% of the theory [$6-^3H$]-6-epigibberellin-$A_3$-7-aldehyde(VII), (specific radioactivity 1.38 mCi/mmol).

Oxydation corresponding to example 1 produces [$6-^3H$]-gibberellin-$A_3$(VIII) (specific radioactivity 1.32 mCi/mmol) and [$6-^3H$]-6-epigibberellin-$A_3$(IX) (specific radioactivity 1.21 mCi/mmol).

EXAMPLE 6

Analogous to example 1, 3.3 mg (0.01 mmol) [$17-^{14}C$]-gibberellin-$A_3$-7-aldehyde (specific radioactivity 0.23 mCi/mmol) are silylated, and enolized with 4 mg potassium hydride. Thereafter, 0.1 ml $^3H_2O$ (specific radioactivity 3 mCi/mmol) are added. Analogous concluding treatment and thin-layer chromatography will produce [$17-^{14}C$, $6_{14}-^3H$]-gibberellin-$A_3$-7-aldehyde (specific radioactivity $^{14}C$: 0.23 mCi/mmol, specific radioactivity $^3H$: 1.39 mCi/mmol) and [$17-^{14}C$, $c-^3H$]-6-epigibberellin-$A_3$-7-aldehyde (specific radioactivity $^{14}C$: 0.20 mCi/mmol; specific radioactivity $^3H$: 1,44 mCi/mmol).

EXAMPLE 7

To 3.48 g (10 mmol) gibberellin-$A_1$(XVI), dissolved in 20 ml absolute pyridin, 20 ml acetic anhydride are added. After letting stand at room temperature for one week, chromatography is performed with chloroform is eluting medium. 3.37 g ≙ 78% of the theoretical value are obtained of the known 0(3),0(13)-diacetyl-gibberellin-$A_1$.

1.73 g (4 mmol) 0(3),0(13)-diacetyl-gibberellin-$A_1$ are dissolved in respectively 10 ml absolute THF and 10 ml absolute dioxane, and combined at −15° C., with 413 mg (2 mmol) DCC. After standing for 12 hours at +5° C., filtration is made from dicyclohexyl urea and the solution combined with 454 mg (12 mmol) $NaBH_4$. After standing for two hours, 2 ml glacial acetic acid are added and concentration is made in vacuum. After addition of ether, shaking out is performed for ten times with a saturated solution of $NaHCO_3$. The residue of the ether phase, dried with $Na_2SO_4$, is chromatographed with chloroform as eluting medium. 553 mg ≙ 66% of the theoretical value, are obtained, of 0(3),0(13)-diacetyl-6β-hydroxymethyl-7-nor-gibberellin-$A_1$.

The acidulated aqueous phases will yield, after extraction with ether and chromatography with chloroform as eluting medium, 733 mg ≙ 85% of the theoretical value 0(3),0(13)-diacetyl-gibberellin-$A_1$.

418.5 mg (0 mmol) 0(3),0(13)-diacetyl-6β-hydroxymethyl-7-nor-gibberellin-$A_1$, dissolved in 5 ml dry $CH_2Cl_2$ are dripped, at room temperature and under argon, into 431.2 mg (2 mmol) pyridinium chlorochromate in 5 ml dry $CH_2Cl_2$. After stirring for two hours, the mixture is combined with 50 ml ether. After separation of the ether phase, the residue is extracted several times with fresh ether. The combined ether extracts are eluted several times with water, dried with $Na_2SO_4$ and concentrated in vacuum. Chromatography of the residue yields, on elution with n-hexane/chloroform, 4:6 vol/vol, 280.2 mg ≙ 73% of the theoretical value 0(3),0(13)-diacetyl-gibberellin-$A_1$-7-aldehyde: amorphous; $[\alpha]_D^{25}+42.2°$ (c=0.42 ethanol);

MS: m/e 416 ($M^+$ or $M^-$ respectively).

With chloroform as elutriant, 32.2 mg of non-converted 0(3),0(13)-diacetyl-6-hydroxymethyl-7-nor-gibberellin-$A_1$ are furthermore obtained.

208.2 mg (0.5 mmol) 0(3),0(13)-diacetyl-gibberellin-$A_1$-7-aldehyde are deacylated with 5 ml of a 0.2 n solution of $NaOCH_3$. After standing at room temperature for three hours, acidulation is made with glacial acetic acid, concentration performed in vacuum and the residue dissolved in ethyl acetate is shaken out with a saturated solution of $NaHCO_3$. After drying of the organic phase with $Na_2SO_4$ concentration in vacuum and chromatographing the residue after elution with chloroform, a yield is obtained of 12.2 mg 0(13)-acetyl-gibberellin-$A_3$-7-aldehyde, and, with a gradient of chloroform/ethyl acetate 8:2 vol/vol, of 71.5 mg ≙ 46% of the theoretical value, gibberellin-$A_1$-7-aldehyde: amorphous; $[\alpha]_D^{25}$ +63.4° (c=0.33 ethanol);

MS: m/e 332 ($M^+$ or $M^-$ respectively)

IR ($CHCl_3$): $\nu_{max}$ 3610 (OH), 2820, 2725 and 1725 (aldehyde) and 1770 $cm^{-1}$ ($\gamma$-lactone-CO).

To 332.4 mg (1 mmol) gibberellin-$A_1$-7-aldehyde, dissolved in 15 ml absolute pyridin, 2 ml hexamethyl disilazane and 2 ml trimethyl chlorosilane are added. After standing at room temperature for three hours, concentration in vacuum is made. After addition of a saturated solution of $NaHCO_3$ exhaustive shaking out with ether is performed. The combined ether phases are dried with anhydrous $MgSO_4$ and concentrated in vacuum. The residue is left standing for 16 hours over $P_4O_{10}$ in vacuum. Subsequently the silylated gibberellin-$A_1$-7-aldehyde is dissolved under argon in 8 ml oxygen-free and absolute THF and 44 mg (1.1 mmol) KH are added at room temperature. After stirring for one hour at room temperature, 0.1 ml (5.55 mmol) $^3H_2O$ (specific radioactivity 3 mCi/mmol) are added to the enolate.

Stirring is continued for another three minutes and 1 ml glacial acetic acid is then added. Repeated concentration in vacuum and repeated addition of methanol allows the removal of unstable tritium. In order to split-off the protective groups, 8 ml THF, 2 ml $H_2O$ and 1 ml glacial acetic acid are then added to the residue, and the whole left standing overnight. After concentration in vacuum, a saturated solution of $NaHCO_3$ is added and shaken out several times with ethyl acetate. Drying of the organic phase with $Na_2SO_4$ and concentration in vacuum will produce a residue that is chromatographed. Elution with chloroform/ethyl acetate 8:2 vol/vol, yields 93 mg ≙ 28% of the theoretical value, of [6-$^3$H]-gibberellin-$A_1$-7-aldehyde and elution with chloroform/ethyl acetate 7:3 vol/vol yields 150 mg ≙ 28% of the theoretical value of [6-$^3$H]-6-epigibberellin-$A_1$-7-aldehyde. [6-$^3$H]-gibberellin-$A_1$-7-aldehyde:

Specific radioactivity 1.32 mCi/mmol; amorphous: $[\alpha]_D^{25}$+62.6° (c=0.43-ethanol);

MS: m/e 332 ($M^+$ or $M^-$ respectively):

IR ($CHCl_3$): $\nu_{max}$ 3610 (OH), 2820, 2725 and 1725 (aldehyde) and 1770 $cm^{-1}$ ($\gamma$-lactone-CO).

[6-$^3$H]-6-epigibberellin-$A_1$-7-aldehyde:

Specific radioactivity 1.48 mCi/mmol; amorphous: $[\alpha]_D^{25}$ −3.8° (c=0.38-ethanol);

MS: m/e 332 ($M^+$ or $M^-$ respectively).

IR($CHCl_3$): 3605 (OH), 2725 and 1725 (aldehyde), 1775 ($\gamma$-lactone-CO) and 1665 $cm^{-1}$ (=$CH_2$).

332.4 mg (1 mmol) [6-$^3$H]-gibberellin-$A_1$-7-aldehyde (specific radioactivity 1.32 mCi/mmol) are acetylated with 3 ml acetic anhydride in 3 ml pyridin. Concentration in vacuum is made after two hours and the crude [6-$^3$H]-O(3)-acetyl-gibberellin-$A_1$-7-aldehyde is dissolved in 8 ml absolute pyridin and combined, under stirring, with 200 mg (2 mmol) $CrO_3$. After stirring for two hours, concentration is made, ether added and repeated shaking-out with 2% HCl then performed.

The residue of the ether phase that has been dried and concentrated with $Na_2SO_4$, is deacylated with 10 ml of a 0.2 n solution of $NaOCH_3$. After standing at room temperature for 15 minutes, acidulation with glacial acetic acid and concentration in vacuum are made, 2% HCl added and extraction with ethyl acetate performed. The residue, after drying with $Na_2SO_4$ and concentration of the organic phase, is then chromatographed. Elution with chloroform/ethyl acetate 8:2 vol/vol produces 61.7 mg unreacted [6-$^3$H]-gibberellin-$A_1$-7-aldehyde. With a gradient of chloroform/ethyl acetate 4:6 vol/vol, a yield is obtained of 210 mg ≙ 74% of the theoretical value [6-$^3$H]-gibberellin-$A_1$: Specific radioactivity 1.14 mCi/mmol; Melting point: 256°–259° C. (from ethyl acetate/n-hexane); $[\alpha]_D^{25}$+35.8° (c=0.52-ethanol);

MS: m/e 348 ($M^+$ or $M^-$ respectively);

IR (Nujol): $\nu_{max}$ 3390 (br, OH), 1745 ($\gamma$-lactone-CO), 1710 (acid-CO) and 1660 $cm^{-1}$ (=$CH_2$).

To oxidize 33.4 mg (1 mmol) [6-$^3$H]-6-epigibberellin-$A_1$-7-aldehyde (specific radioactivity 1.48 mCi/mmol), acetylation is first made with 3 ml acetic anhydride in 3 ml absolute pyridin. Concentration in vacuum is made after two hours and the crude [6-$^3$H]-O(3)-acetyl-6-epigibberellin-$A_1$-7-aldehyde is dissolved in 8 ml absolute pyridin and combined under stirring with 300 mg (3 mmol) $CrO_3$. Concentration is made after 18 hours, ethyl acetate added and repeated shaking out with 2% HCl made. The residue of the organic phase that has been dried and concentrated with $Na_2SO_4$, is deacylated with 10 ml of a 0.2 n solution of $NaOCH_3$. After standing at room temperature for 15 minutes, acidulation with glacial acetic acid and concentration in vacuum are made, 2% HCl added, extraction with ethyl acetate performed. The residue after drying with $Na_2SO_4$ and concentration of the organic phase, is chromatographed. On elution with chloroform/ethyl acetate 7:3 vol/vol, 68.2 mg [6-$^3$H]-6-epigibberellin-$A_1$-7-aldehyde are returned. With a gradient of chloroform-/ethyl acetate 3:7 vol/vol, elution will yield 117.1 mg ≙ 42% of the theoretical value, [6-$^3$H]-6-epigibberellin-$A_1$: specific radioactivity 1,26 mCi/mmol;

Amorphous:

$[\alpha]_D^{25}$−8.6° (c=0.53-ethanol);

MS: m/e 348 ($M^+$ or $M^-$ respectively);

IR (Nujol): $\nu_{max}$ 3410 (br, OH), 1720 (acid-CO) and 1755 $cm^{-1}$ ($\gamma$-lactone-CO).

EXAMPLE 8

To 1.1 g (3.33 mmol) gibberellin-$A_5$(XVII), dissolved in 10 ml absolute THF and 10 ml absolute dioxane, 343 mg (1.66 mmol) DDC are added at −15° C. After standing at +5° C. for 12 hours, filtration is made from dicyclohexyl urea and the solution combined with 378 mg (10 mmol) $NaBH_4$. Allowing the reaction for two hours, 2 ml glacial acetic acid are then added and concentration in vacuum made. After the addition of ether, shaking out with a saturated solution of $NaHCO_3$ is made ten times. The residue of the ether phase, dried with $Na_2SO_4$ is chromatographed, wherein elution with chloroform/ethyl acetate 7:3 vol/vol yields 353 mg ≙ 67% of the theoretical value, of 6$\beta$-hydroxymethyl-7-nor-gibberellin-$A_5$.

The acidulated aqueous phases yield, after extraction with ether, and chromatography with chloroform-/ethyl acetate 9:1 or 8:2 respectively, vol/vol, 446 mg ≙ 87% of the theoretical value, gibberellin-$A_5$.

To 323 mg (1.5 mmol) pyridinium chlorochromate in 5 ml dry $CH_2Cl_2$, a solution of 316.4 mg (1 mmol) 6$\beta$-hydroxyethyl-7-nor-gibberellin-$A_5$ in 5 ml dry $CH_2Cl_2$ are dripped-in while stirring under an argon atmosphere. Furthermore, 100 mg sodium acetate are added as buffer. After two hours, the mixture is combined with 50 ml ether. After separation of the ether phase, the residue is extracted repeatedly with fresh ether. The combined ether extracts are eluted repeatedly with water, dried with $Na_2SO_4$ and concentrated in vacuum. Subsequent chromatography of the residue will yield on elution with n-hexane/chloroform 1:4 vol/vol, 222.3 mg ≙ 79% of the theoretical value, gibberellin-$A_5$-7-aldehyde:

Amorphous:

MS: m/e 314 ($M^+$ or $M^-$ respectively);

IR ($CHCl_3$): $\nu_{max}$ 3605 OH, 2725 and 1725 (aldehyde) and 1775 $cm^{-1}$ (γ-lactone-CO).

On elution with chloroform/ethyl acetate 7:3 vol/vol, 33.3 mg unreacted 6β-Hydroxy-methyl-7-nor-gibberellin-$A_5$ are furthermore obtained.

To 314.4 mg (1 mmol) gibberellin-$A_5$-7-aldehyde, dissolved in 15 ml absolute pyridin, 2 ml hexamethyldisilazane and 2 ml trimethylchlorosilan are added. After standing at room temperature for three hours, concentration in vacuum is made. After the addition of a saturated solution of $NaHCO_3$, through shaking-out with ether is performed. The residue is left standing overnight in vacuum over $P_4O_{10}$. The combined ether phases are dried with anhydrous $MgSO_4$ and concentrated in vacuum. The silylated gibberellin-$A_5$-7-aldehyde is subsequently dissolved under argon in 8 ml oxygen-free and absolute THF, and 44 mg (1 mmol) KH are added at room temperature. After stirring at room temperature for one hour, 0.1 ml (5.55 mmol) $^3H_2O$ (specific radioactivity 3 mCi/mmol) are added to the enolate. Stirring is made for another three minutes and then combination with 1 ml glacial acetic acid. Repeated concentration in vacuum and repeated addition of methanol make possible the removal of unstable tritium.

To separate the silyl group, the residue is dissolved in 8 ml THF, 2 ml $H_2O$ and 1 ml glacial acetic acid are added and the whole left standing overnight. After concentration in vacuum, a saturated solution of $NaHCO_3$ is added and repeated shaking-out with ethyl acetate performed. Drying of the organic phase with $Na_2SO_4$ and concentration in vacuum, produces a residue which is subsequently chromatographed.

Elution with n-hexane/chloroform 1:9 vol/vol yields 101 mg ≙ 32% of the theoretical value [6-$^3$H]-gibberellin-$A_5$-7-aldehyde, and elution with chloroform yields 153 mg ≙ 49% of the theory [6-$^3$H]-6-epigibberellin-$A_5$-7-aldehyde.

[6-$^3$H]-gibberellin-$A_5$-7-aldehyde:

Specific radioactivity 1.39 mCi/mmol; amorphous;

MS: m/e 314 ($M^+$ or $M^-$ respectively) [6-$^3$H]-6-epigibberellin-$A_5$-7-aldehyde:

Specific radioactivity 1.5 cmCi/mmol; amorphous;

MS: m/e 314 ($M^+$ or $M^-$ respectively).

314.4 mg (1 mmol) [6-$^3$H]-gibberellin-$A_5$-7 aldehyde (specific radioactivity 1.39 mCi/mmol) are dissolved in 8 ml absolute pyridin and combined under stirring with 200 mg (2 mmol) $CrO_3$. After stirring for two hours, concentration is made in vacuum, ethyl acetate added and repeated shaking out with 2% HCl performed. The residue of the organic phase, that had been dried with $Na_2SO_4$ and concentrated, is subsequently chromatographed. Elution with n-hexane chloroform 1:9, vol/vol produces 42.1 mg unreacted [6-$^3$H]-gibberellin-$A_5$-7-aldehyde. With a gradient of chloroform/ethyl acetate 8:2 vol/vol, a yield is obtained of 224.3 mg ≙ 80% of the theoretical value [6-$^3$H]-gibberellin-$A_5$:

Specific radioactivity 1.31 mCi/mmol;

Melting point: 260°-261° C.

$[\alpha]_D^{25}-76.2°$ (c=0.58-ethanol):

MS: m/e 330 ($M^+$ or $M^-$ respectively)

IR (Nujol): $\nu_{max}$ 3430 (br, OH), 1765 (γ-lactone-CO) and 1660 $cm^{-1}$ (=$CH_2$).

To 314.4 mg (1 mmol) [6-$^3$H]-6-epigibberellin-$A_5$-7-aldehyde (specific radioactivity 1.5 mCi/mmol), dissolved in 8 ml absolute pyridin, 300 mg (3 mmol) $CrO_3$ are added. After stirring for 18 hours, concentration is made in vacuum and repeated shaking with 2% HCl performed. The residue of the organic phase that had been dried with $Na_2SO_4$ and concentrated, is subsequently chromatographed. Elution with chloroform produces 26.3 mg unreacted [6-$^3$H]-6-epigibberellin-$A_5$-7-aldehyde. With a gradient of chloroform/ethyl acetate 7:3 vol/vol, a yield is obtained of 166.8 mg ≙ 55% of the theoretical value, [6-$^3$H]-6-epigibberellin-$A_5$: Specific radioactivity 1.38 mCi/mmol; amorphous; $[\alpha]_D^{25}-112.1°$ (c=0.48-ethanol);

MS: m/e 330 ($M^+$ or $M^-$ respectively).

EXAMPLE 9

To 127 mg (0.4 mmol) gibberellin-$A_9$(XVIII), dissolved in 2 ml absolute THF and 2 ml absolute dioxane, 41.3 mg (0.2 mmol) DCC are added at −15° C. After 12 hours standing at +5° C., filtration is made from dicyclohexyl urea and the solution combined with 45.4 mg (1.2 mmol) $NaBH_4$. Allowing two hours for reacting, 1 ml glacial acetic acid is then added and concentration in vacuum performed thereupon. After the addition of ether, shaking-out with ether is performed 10 times. The residue of the ether phase that had been dried with $Na_2SO_4$ is chromatographed, wherein, an elution with n-hexane/chloroform 6:4 vol/vol, a yield is obtained of 41.2 mg ≙ 68% of the theoretical value, of 6β-Hydroxymethyl-7-nor-gibberellin-$A_9$.

The acidulated aqueous phases will yield, after extraction with ether and chromatography with n-hexane/chloroform 2:8 vol/vol, 52.2 mg ≙ 82% of the theoretical value, gibberellin-$A_9$.

To 56 mg (0.26 mmol) pyridinium chlorochromate and 50 mg sodium acetate in 1 ml dry $CH_2Cl_2$, a solution of 39.3 mg (0.13 mmol) 6β-Hydroxymethyl-7-nor-gibberellin-$A_9$ in 1 ml dry $CH_2Cl_2$ is dripped-in with stirring and in an argon atmosphere. After two hours, the mixture is combined with 20 ml ether. After separation of the ether phase, the residue is repeatedly extracted with fresh ether. The combined ether extracts are repeatedly eluted with water, dried with $Na_2SO_4$ and concentrated in vacuum. Subsequent chromatography will yield, on elution with n-hexane/chloroform 8:2, vol/vol, 30 mg ≙ 77% of the theoretical value gibberellin-$A_9$-7-aldehyde: amorphous;

MS: m/e 300 ($M^+$ or $M^-$ respectively)

IR ($CHCl_3$): $\nu_{max}$ 2725 and 1725 (aldehyde) and 1775 $cm^{-1}$ (γ-lactone-CO).

To 30.0 mg (0.1 mmol) gibberellin-$A_9$-7-aldehyde dissolved in 1 ml absolute THF, 8 mg (0.2 mmol) KH are added at room temperature in an argon atmosphere. After stirring at room temperature for one hour, 0.01 ml (0.56 mmol) $^3H_2O$ (specific radioactivity 3 mCi/mmol) is added to the enolate.

Stirring is continued for a further three minutes and combinning is made with 0.1 ml glacial acetic acid. Repeated concentration in vacuum and repeated addition of methanol make possible the removal of unstable tritium. Water is then added to the residue and thorough extraction with ether performed. Drying of the organic phase with $Na_2SO_4$ and concentration in vacuum produce a residue that is subsequently chromatographed. Elution with n-hexane/chloroform 1:1 vol/vol yields 9.9 mg ≙ 33% of the theoretical value [6-$^3$H]-gibberellin-$A_9$-7-aldehyde, and on elution with n/hexane/chloroform 4:6 vol/vol, one obtains 13.8 mg ≙ 46% of the theoretical value [6-$^3$H]-6-epigibberellin-$A_9$-7-aldehyde. [6-$^3$H]-gibberellin-$A_9$-7-aldehyde:

Specific radioactivity 1.42 mCi/mmol; amorphous;
MS: m/e 300 ($M^+$ or $M^-$ respectively);
IR ($CHCl_3$): $\nu_{max}$ 2725 and 1725 (aldehyde) and 1775 $cm^{-1}$ (γ-lactone-CO); [6-$^3$H]-6-epigibberellin-$A_9$-7-aldehyde:

Specific radioactivity 1.5 mCi/mmol; amorphous;
MS: m/e 300 ($M^+$ or $M^-$ respectively);
IR ($CHCl_3$): $\nu_{max}$ 2725 and 1725 (aldehyde) and 1775 $cm^{-1}$ (γ-lactone-CO).

9.0 mg (0.03 mmol) [6-$^3$H]-gibberellin-$A_9$-7-aldehyde (specific radioactivity 1.42 mCi/mmol) are dissolved in 1 ml absolute pyridin and combined under stirring with 10 mg (0.1 mmol) $CrO_3$. After stirring for two hours, concentration in vacuum is performed, ether added and repeated shaking out with 2% HCl performed. The residue of the ether phase that had been dried with $Na_2SO_4$ and concentrated, is then purified by thin-layer chromatography. One•obtains 6.9 mg ≙ 73% of the theoretical value [6-$^3$H]-gibberellin-$A_9$:

Specific radioactivity 1.37 mCi/mmol;
Melting point: 208°-211° C. (Chloroform/n-hexane);
$[\alpha]_D^{25}$ −24.9° (c—0.53-ethanol);
MS: m/e 316 ($M^+$ or $M^-$ respectively);
IR ($CHCl_3$): $\nu_{max}$ 1760 (-lactone-CO), 1705 (acid-CO) and 1655 $cm^{-1}$ (=$CH_2$).

To 12.0 mg (0.04 mmol) [6-$^3$H]-6-epigibberellin-$A_9$-7-aldehyde (specific radioactivity 1.5 mCi/mmol), 1 ml absolute pyridin and 20 mg (0.2 mmol) $CrO_3$ are added. After stirring for 15 hours, concentration in vacuum is made, ether added and repeated shaking-out with 2% HCl performed. The residue of the ether phase that had been dried with $Na_2SO_4$ and concentrated, is then purified by thin-layer chromatography. Isolation yields 5.1 mg ≙ 40% of the theoretical value, [6-$^3$H]-6-epigibberellin-$A_9$: Specific radioactivity 1.43 mCi/mmol; amorphous;

MS: m/e 316 ($M^+$ or $M^-$ respectively);
IR ($CHCl_3$): $\nu_{max}$ 1765 (γlactone-CO), 1705 (acid-CO) and 1655 $cm^{-1}$ (=$CH_2$).

EXAMPLE 10

Analogous to example, gibberellin-$A_4$(XIX) is prepared by acetylizing O(3)-acetyl-gibberellin-$A_4$. Subsequent reaction with DCC and $NaBH_4$ produces O(3)-acetyl-6β-hydroxymethyl-7-nor-gibberellin-$A_4$. By oxydation with pyridinium chlorochromate, O(3)-acetyl-gibberellin-$A_4$-7-aldehyde is obtained. Gibberellin-$A_4$-7-aldehyde is synthesized by deacetylation and then silylated, enolized with KH and reacted with $^3H_2O$ to [6-$^3$H]-gibberellin-$A_4$-7-aldehyde and [6-$^3$H]-6-epigibberellin-$A_4$-7-aldehyde. Analogous oxydation produces [6-$^3$H]-gibberellin-$A_4$:

Specific radioactivity 1.27 mCi/mmol;
Melting point: 215°-216° C. (from ethyl ethyl acetate/n-hexane);
$[\alpha]_D^{25}$ −5.1° (c=0.50—ethanol);
MS: m/e 332 ($M^+$ or $M^-$ respectively);
IR (Nujol): $\nu_{max}$ 3410 (br, OH), 1760 (γ-lactone-CO) and 1710 $cm^{-1}$ (acid-CO).

EXAMPLE 11

Analogous to example 1, acetylation of gibberellin-$A_7$(XX) produces O(3)-acetyl-gibberellin-$A_7$. Subsequent reaction with DCC and $NaBH_4$ produces O(3)-acetyl-6β-hydroxymethyl-7-nor-gibberellin-7. O(3)-acetyl-gibberellin-$A_7$-7-aldehyde is synthesized with pyridinium chlorochromate as oxydant. Deacetylation produces gibberellin-$A_7$-7-aldehyde which, silylated and enolized with KH will react with $^3H_2O$ to [6-$^3$H]-gibberellin-$A_7$-7-aldehyde and [6-$^3$H]-6-epigibberellin-$A_7$-7-aldehyde. Analogous oxidation produces [6-$^3$H]-gibberellin-$A_7$:

Specific radioactivity 1.29 mCi/mmol;
Melting point: 170°-172° C. (from ethyl acetate/n-hexane);
$[\alpha]_D^{25}$ +21.2° (c=0.58-ethanol);
IR (Nujol): $\nu_{max}$ 3400 (br, OH), 1755 (γlactone-CO) and 1715 $cm^{-1}$ (acid-CO).

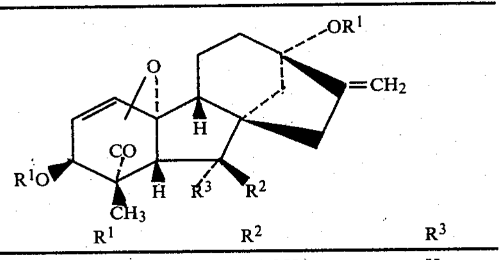

| | $R^1$ | $R^2$ | $R^3$ |
|---|---|---|---|
| I | H | COOH | H |
| II | Ac | COOH | H |
| III | Ac | $CH_2OH$ | H |
| IV | Ac | CHO | H |
| V | H | CHO | H |
| VI | H | CHO | $^3$H |
| VII | H | $^3$H | CHO |
| VIII | H | COOH | $^3$H |
| IX | H | $^3$H | COOH |
| X | H | CHO | $^2$H |
| XI | H | $^2$H | CHO |
| XII | H | COOH | $^2$H |
| XIII | H | $^2$H | COOH |
| XIV | H | H | CHO |
| XV | H | H | COOH |

XVI

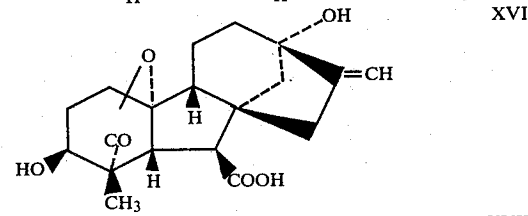

XVII

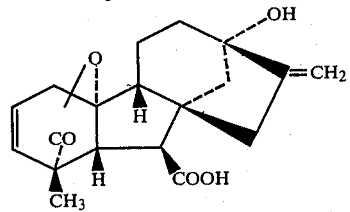

XVIII

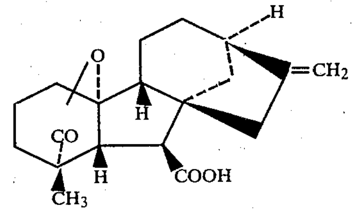

XIX

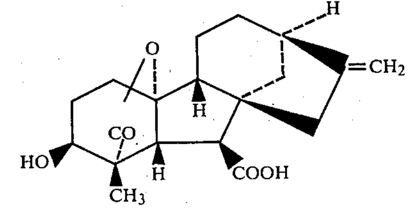

-continued
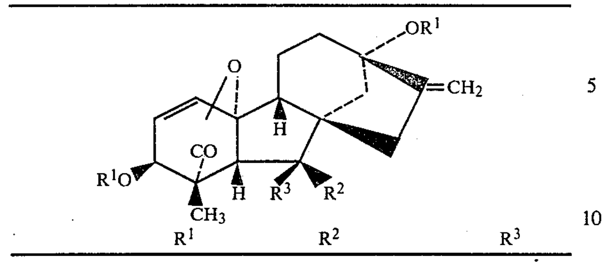
| $R^1$ | $R^2$ | $R^3$ |
|---|---|---|
| | | XX |
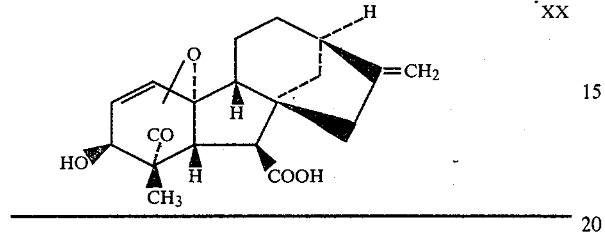
We claim:
1. [6-$^3$H]-6-Epigibberellines.
2. [6-$^3$H]-Gibberellin-$A_1$.
3. [6-$^3$H]-Gibberellin-$A_3$.
4. [6-$^3$H]-Gibberellin-$A_4$.
5. [6-$^3$H]-Gibberellin-$A_5$.
6. [6-$^3$H]-Gibberellin-$A_7$.
7. [6-$^3$H]-Gibberellin-$A_9$.
8. [6-$^3$H]-6-Epigibberellin-$A_1$.
9. [6-$^3$H]-6-Epigibberellin-$A_3$.
10. [6-$^3$H]-6-Epigibberellin-$A_4$.
11. [6-$^3$H]-6-Epigibberellin-$A_5$.
12. [6-$^3$H]-6-Epigibberellin-$A_7$.
13. [6-$^3$H]-6-Epigibberellin-$A_9$.
* * * * *

UNITED STATES PATENT AND TRADEMARK OFFICE

CERTIFICATE OF CORRECTION

PATENT NO. : 4,282,154

DATED : August 4, 1981

INVENTOR(S) : Manfred Lischewski and Günter Adam

It is certified that error appears in the above-identified patent and that said Letters Patent are hereby corrected as shown below:

In the heading:

[75] The address of the second inventor, Günter Adam, should read -- Halle (Saale) --.

[73] The name of the Assignee should read -- Akademie der Wissenschaften der DDR --.

Signed and Sealed this

*Twenty-sixth* Day of *January 1982*

[SEAL]

*Attest:*

GERALD J. MOSSINGHOFF

*Attesting Officer* *Commissioner of Patents and Trademarks*